United States Patent
Gutenev (10) Patent No.: US 7,248,724 B2
(45) Date of Patent: Jul. 24, 2007

(54) METHOD FOR MONITORING WOUNDS

(75) Inventor: Alexander Gutenev, North Narrabeen (AU)

(73) Assignee: Polartechnics Limited, Sydney, NSW (AU)

( * ) Notice: Subject to any disclaimer, the term of this patent is extended or adjusted under 35 U.S.C. 154(b) by 803 days.

(21) Appl. No.: 10/712,733

(22) Filed: Nov. 12, 2003

(65) Prior Publication Data

US 2004/0136579 A1    Jul. 15, 2004

(51) Int. Cl.
*G06K 9/00* (2006.01)
(52) U.S. Cl. ................................ 382/128; 382/199
(58) Field of Classification Search ........... 382/128, 382/133, 134, 199
See application file for complete search history.

(56) References Cited

U.S. PATENT DOCUMENTS

| | | | | |
|---|---|---|---|---|
| 5,588,428 A * | 12/1996 | Smith et al. | ........... | 600/425 |
| 6,081,612 A * | 6/2000 | Gutkowicz-Krusin et al. | ... | 382/128 |
| 6,381,026 B1 * | 4/2002 | Schiff et al. | ........... | 356/601 |
| 6,413,212 B1 * | 7/2002 | Raab | ........... | 600/300 |
| 6,757,413 B1 * | 6/2004 | LeMahieu | ........... | 382/128 |

OTHER PUBLICATIONS

Nischik and Forster Analysis of Skin Erythema Using True-Color Images, IEEE Transactions on Medical Imaging, vol. 16, No. 6 Dec. 1997 pp. 711-716.
Herbin et al. Assessment of Healing Kinetics Through True Color Image Processing, IEEE Transactions on Medical Imaging, vol. 12, No. 1 Mar. 1993, pp. 39-43.
Mekkes et al. Image Processing in the Study of Wound Healing, Kinetics in Dermatology, 1995; 13: 401-407.

* cited by examiner

*Primary Examiner*—Vikkram Bali
(74) *Attorney, Agent, or Firm*—Gottlieb Rackman & Reisman, PC (57) ABSTRACT

A method of quantifying the extent of erythema around a wound of a patient is disclosed. An image (200) is captured that includes the wound, the erythema and surrounding skin. A border of the wound is identified (step 232) and a distance transform is performed (step 234) on an area of the image between the wound border and a boundary of the image to determine bands of pixels (226, 228, 230), wherein the pixels within each band are equidistant from the wound border. A representative value such as average brightness is calculated for each band (step 238), and a threshold level is defined relative to the representative value of the surrounding skin (step 240). The extent of the erythema is then calculated.

18 Claims, 11 Drawing Sheets

METHOD FOR MONITORING WOUNDS

FIELD OF THE INVENTION

The present invention relates generally to the monitoring of wounds and, in particular, to quantifying the extent of erythema around a wound.

BACKGROUND

When a patient suffers a wound to the body, the typical symptoms of inflammation include change of color (erythema), swelling (oedema), local increase in temperature and pain. Most of these symptoms result from changes in blood vessels caused by the release of inflammatory agents at the location of the damaged cells.

From a diagnostic point of view, change of color is one of the most important manifestations of inflammation.

Although the wound healing process is well documented from a physio-chemical perspective, physicians generally base the progress of the healing process on a visual observation of wound color and size. Judgement of changes in the wound is thus subjective, depending on a recollection of the earlier visual appearance of the wound.

A wound is defined as an area of tissue damage typically caused by the impact of a sharp object which may also cause breakage of the skin. The wound is not the total area of erythema, nor is it the erythema resulting from other causes such as an infection.

It is important to detect symptoms of potential complications as soon as possible so that appropriate treatment may be introduced to curtail further development of the complication, which may include infection.

Image processing techniques have been used to track variations in erythema over time. Images of the wound are captured at successive time intervals and processed in color spaces such as CIE L*a*b* for pseudo-perceptual image interpretation. The image is segmented using color to differentiate the erythema and the clear skin. The problem with this approach is the low contrast between the erythema and clear skin at the erythema boundary, which makes it difficult to obtain an accurate segmentation.

Another method of monitoring blood-flow changes such as those causing erythema is laser Doppler flowmetry. However, a laser Doppler perfusion imager (LDPI) registers blood flow only at a single point, so it takes several minutes to build up an image of the entire area of the wound. The method is time consuming compared to image-based techniques, and may inconvenience the patient.

There is accordingly a need for a simple, standardised method of quantifying the extent of erythema.

SUMMARY

It is an object of the present invention to substantially overcome, or at least ameliorate, one or more disadvantages of existing arrangements.

According to a first aspect of the invention there is provided a method of quantifying the extent of erythema around a wound of a patient, the method comprising the steps of:

capturing an image that includes the wound, the erythema and surrounding skin;

defining a border of the wound;

performing a distance transform on an area of the image between the wound border and a boundary of the image to determine bands of pixels, wherein the pixels within each said band are equidistant from the wound border;

calculating a representative value for each said band;

defining a threshold level relative to the representative value of the surrounding skin;

identifying an erythema boundary as the band having a representative value closest to the threshold level; and calculating a characteristic value to quantify the region within the erythema boundary.

According to a second aspect of the invention, there is provided a method of monitoring a wound of a patient, the method comprising the steps of:

capturing a time series of images, each said image including the wound, erythema around the wound and clear skin surrounding the erythema;

for each said image, defining a border of the wound;

for each said image, performing a distance transform on an area of the image between the wound border and a boundary of the image to determine bands of pixels, wherein the pixels within each said band are equidistant from the wound border;

for each image, calculating a representative value for each said band;

defining a threshold level relative to the representative value of the surrounding clear skin;

for each image, identifying an erythema boundary as the band having a representative value closest to the threshold level;

for each image, calculating a characteristic value to quantify the region within the erythema boundary; and comparing said characteristic values to monitor changes in the extent of erythema around the wound.

According to a further aspect of the invention there is provided apparatus for quantifying the extent of erythema in an image including a wound, erythema around the wound and clear skin surrounding the erythema, the apparatus comprising:

means for defining a border of the wound;

means for performing a distance transform on an area of the image between the wound border and a boundary of the image to determine bands of pixels, wherein the pixels within each said band are equidistant from the wound border;

means for calculating a representative value for each said band;

means for identifying an erythema boundary as the band having a representative value closest to a threshold level; and means for calculating a characteristic value to quantify the region within the erythema boundary.

A computer program and a computer readable medium are also disclosed.

BRIEF DESCRIPTION OF THE DRAWINGS

Some aspects of the prior art and one or more embodiments of the present invention will now be described with reference to the drawings, in which.

DETAILED DESCRIPTION INCLUDING BEST MODE

Figure 1:
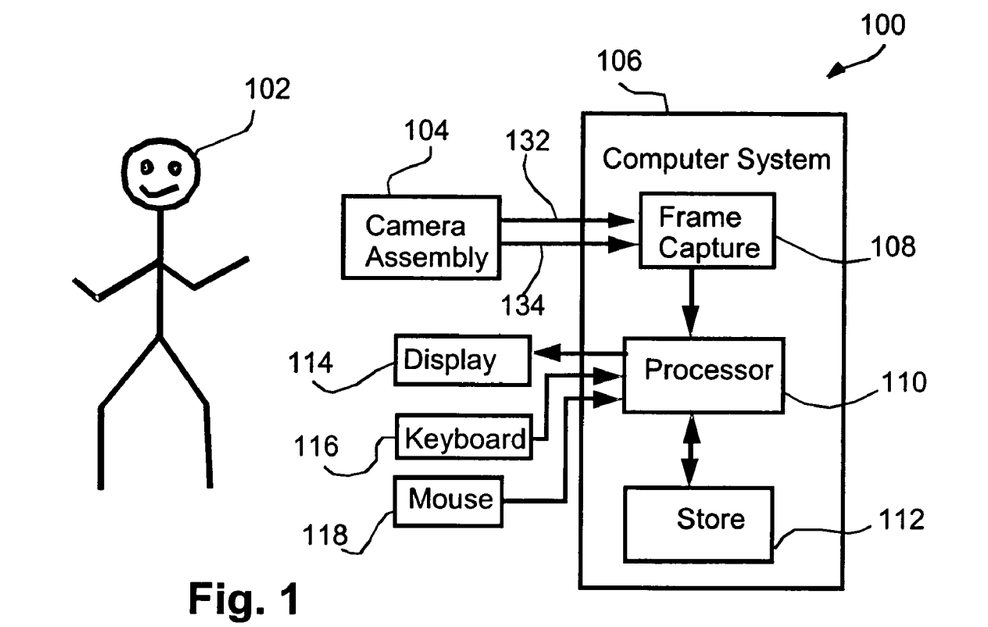
FIG. 1 shows a schematic block diagram of an arrangement for capturing an image of a wound.
Figure 2:
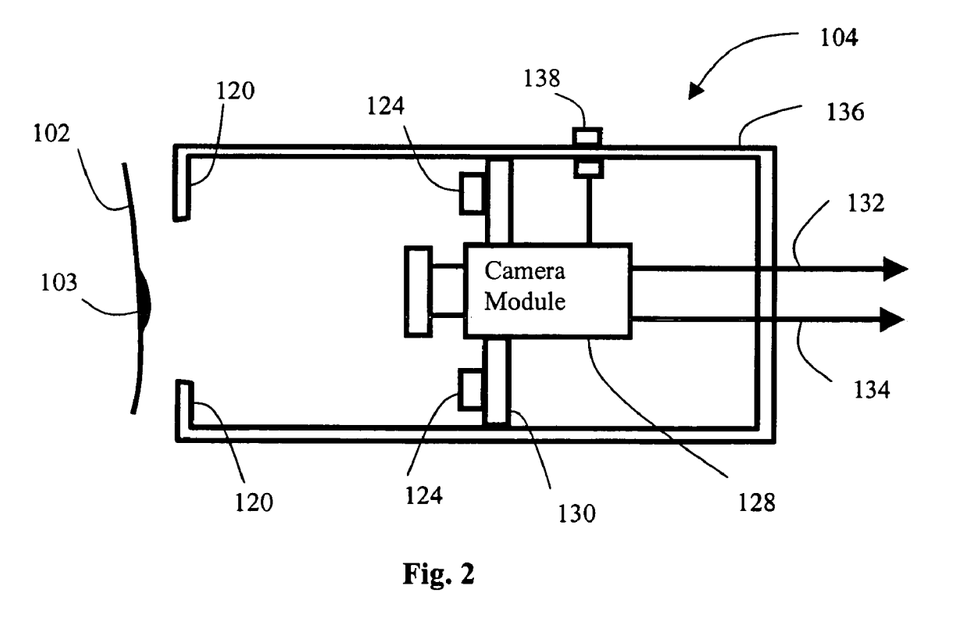
FIG. 2 shows a schematic representation of a camera assembly for use in the arrangement of FIG. 1.

The present disclosure relates to a method for quantifying the extent of erythema surrounding a wound. The described method operates on a captured image that includes the wound to be examined. FIGS. 1 and 2 show a system upon which the methods of the present application may be implemented.

FIG. 1 shows a wound monitoring system 100 in which a camera assembly 104 is directed at a portion of a patient 102 in order to capture an image of the skin of the patient 102 in a region including a wound. The camera assembly 104 couples to a computer system 106 which incorporates a frame capture board 108 configured to capture a digital representation of the image formed by the camera assembly 104. The frame capture board 108 couples to a processor 110 which can operate to store the captured image in a memory store 112 and also to perform various image processing activities on the stored image and variations thereof that may be formed from such processing and/or stored in the memory store 112. Also coupled to the computer system via the processor 110 is a display 114 by which images captured and/or generated by the system 106 may be represented to the user or physician, as well as keyboard 116 and mouse pointer device 118 by which user commands may be input.

As seen in FIG. 2, the camera assembly 104 includes a chassis 136 incorporating a frame 120 which is placed over the region of interest of the patient 102 which, in this case, is seen to incorporate a wound 103.

The camera assembly 104 further includes a camera module 128 mounted within the chassis from supports 130 in such a manner that the camera module 128 is fixed in its focal length upon the frame 120, which is placed against the skin of the patient 102. In this fashion, the optical parameters and settings of the camera module 128 may be preset and need not be altered for the capture of individual images. In the arrangement of FIG. 2, light sources 124 are arrayed around the camera lens to illuminate the skin 102 under examination. Alternatively, the chassis 136 may be made of a transparent material, allowing light from an external source to illuminate the skin 102.

The camera module 128 includes an image data output 132 together with a data capture control signal 134, for example actuated by a user operable switch 138. The control signal 134 may be used to actuate the frame capture board 108 to capture the particular frame image currently being output on the image connection 132. As a consequence, the physician using the system 100 has the capacity to move the camera assembly 104 about the patient and into an appropriate position over the wound 103 and when satisfied with the position (as represented by a real-time image displayed on the display 114), may capture the particular image by depression of the switch 138 which actuates the control signal 134 to cause the frame capture board 108 to capture the image.

Because specular reflection caused by the surface skin layer (stratum corneum) can produce noise in the captured image, a transparent fluid may be applied to the skin undergoing examination in order to reduce reflection. Gels such as KY Jelly™, produced by Johnson and Johnson of New Brunswick, N.J., USA, have been found to be easy to apply and effective in reducing reflection noise.

Figure 7:
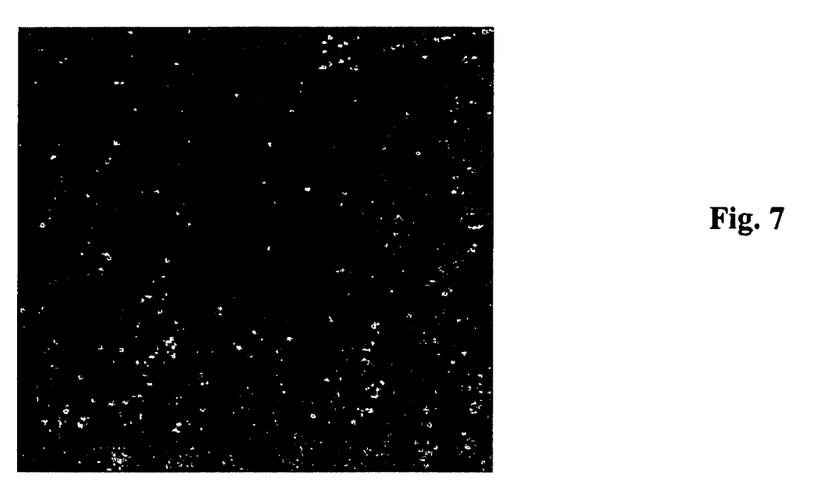
FIG. 7 shows an image of a wound.
Figure 8:
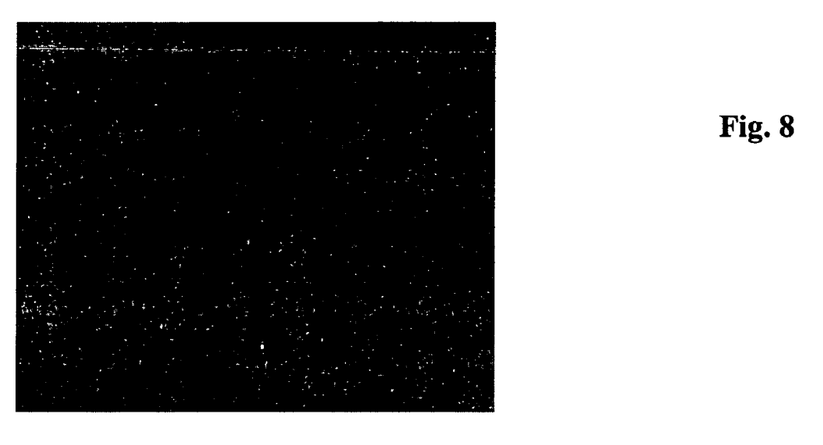
FIG. 8 shows an image of a wound with a fluid applied to the wound to reduce reflection noise.

FIG. 7 is an example of an image of a wound and surrounding skin. Although the detail may be obscured by poor reproduction of the image, FIG. 7 exhibits multiple highlights where the image has saturated due to specular reflection. FIG. 8 shows an image of a wound where KY Jelly has been applied to the patient 102. The image of FIG. 8 is free of specular reflections since the layer of fluid has diverted reflected illumination away from the camera lens. Noise due to skin crevices is also reduced.

As an alternative to the use of clear gels, cross-polarised light may be used to reduce the effect of specular reflection. In this arrangement a polarising filter is fitted to the illumination source and another polarising filter is fitted to the camera lens.

The computer system 106 may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present invention also implicitly discloses a computer program, in that it would be apparent to the person skilled in the art that the individual steps of the preferred method described herein are to be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention. Furthermore one or more of the steps of the computer program may be performed in parallel rather than sequentially.

Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

Where reference is made in any one or more of the accompanying drawings to steps and/or features, which have the same reference numerals, those steps and/or features have for the purposes of this description the same function(s) or operation(s), unless the contrary intention appears.

Figure 3:
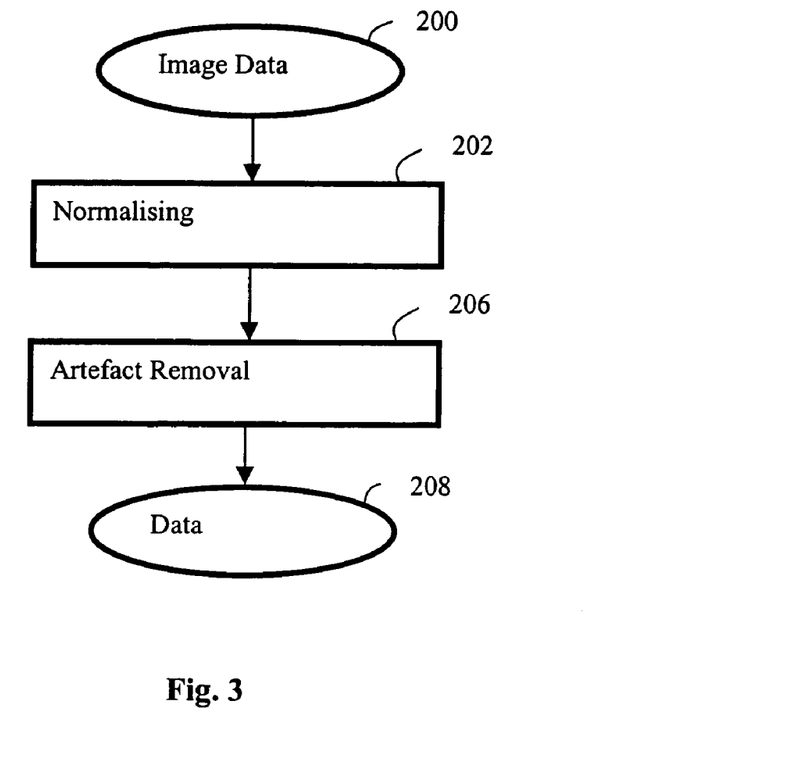
FIG. 3 is a flow chart of preliminary steps used to process image data obtained using the arrangement of FIG. 1.

FIG. 3 is a flow chart of preparatory processing that may be applied to image data 200 captured by the wound monitoring system 100.

Initially, in step 202, image data 200 is subjected to a normalising color tinge correction process which acts to compensate for light variations across the surface of the image.

Next, in step 206, artefacts may be removed from the image data 200. Such artefacts may include bubbles in the gel applied to the skin of the patient 102, or hairs visible in the field of view of the camera assembly 104. Artefact removal is not always necessary. For example, if median brightness measures are used in the method of FIG. 4, then artefact removal is not necessary, whereas artefact removal is required if mean values of brightness are calculated.

The output of the preparatory steps 202-206 is data 208, which is further processed to analyse the wound 103. Normalisation, ie correction for light field irregularities, is necessary for correct wound delineation, since it enables reliable comparison of wounds captured on different patients, or wounds imaged on the same patient at different times. A data-base of wound images taken under comparable conditions may thus be accumulated.

Figure 4:
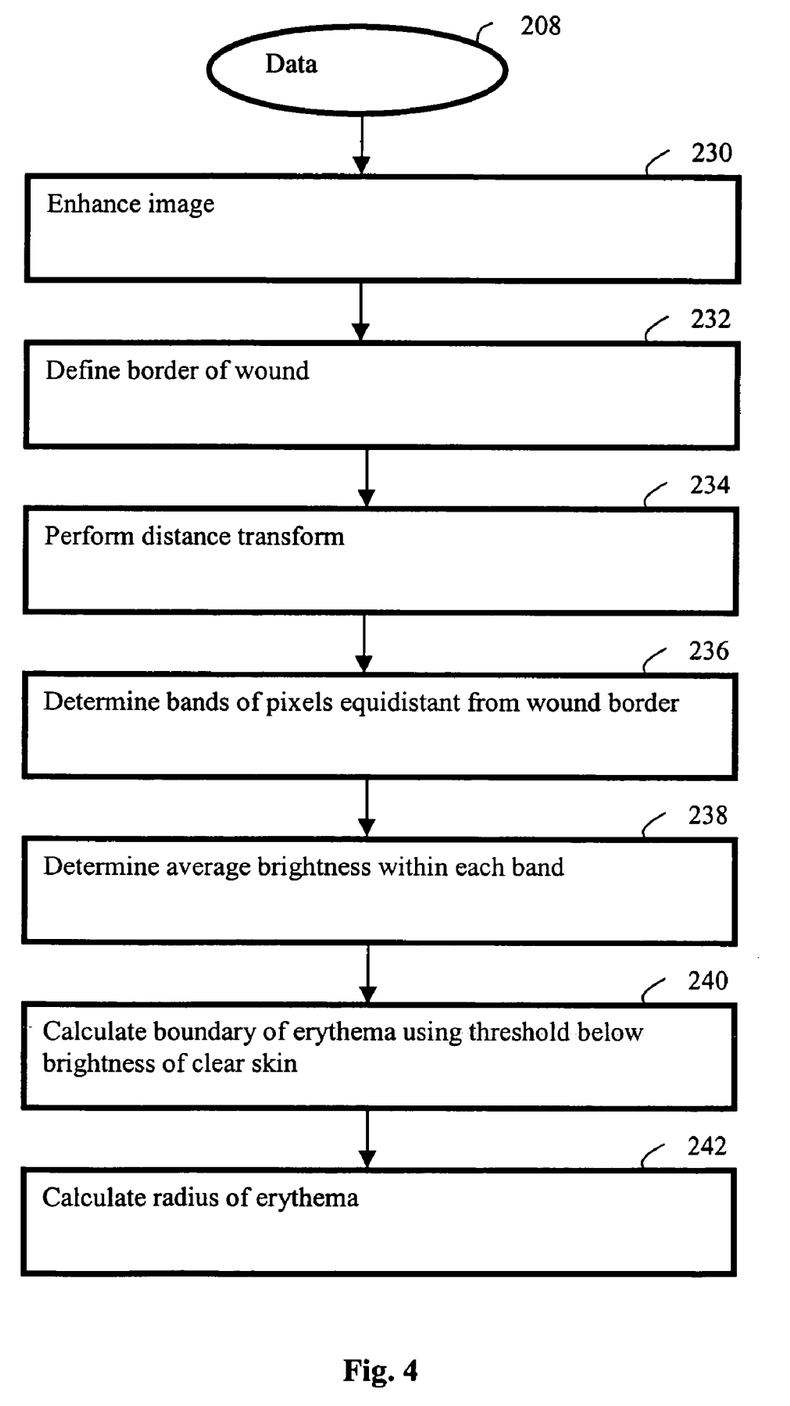
FIG. 4 is a flow chart of a method to quantify the extent of erythema around a wound.

FIG. 4 shows how the data 208 is processed in order to quantify the extent of erythema around the wound 103.

In step 230 the image is enhanced to maximise the contrast between the background skin and the inflamed area around the wound 103. Any suitable technique may be employed, but a preferred method is described below with reference to FIG. 6. The preferred method replaces the intensity component of the image data 208 with a principal component value that captures most of the variance in the data, thereby providing an enhanced contrast. The preferred enhancement method does not introduce any non-linear operations.

Figure 6:
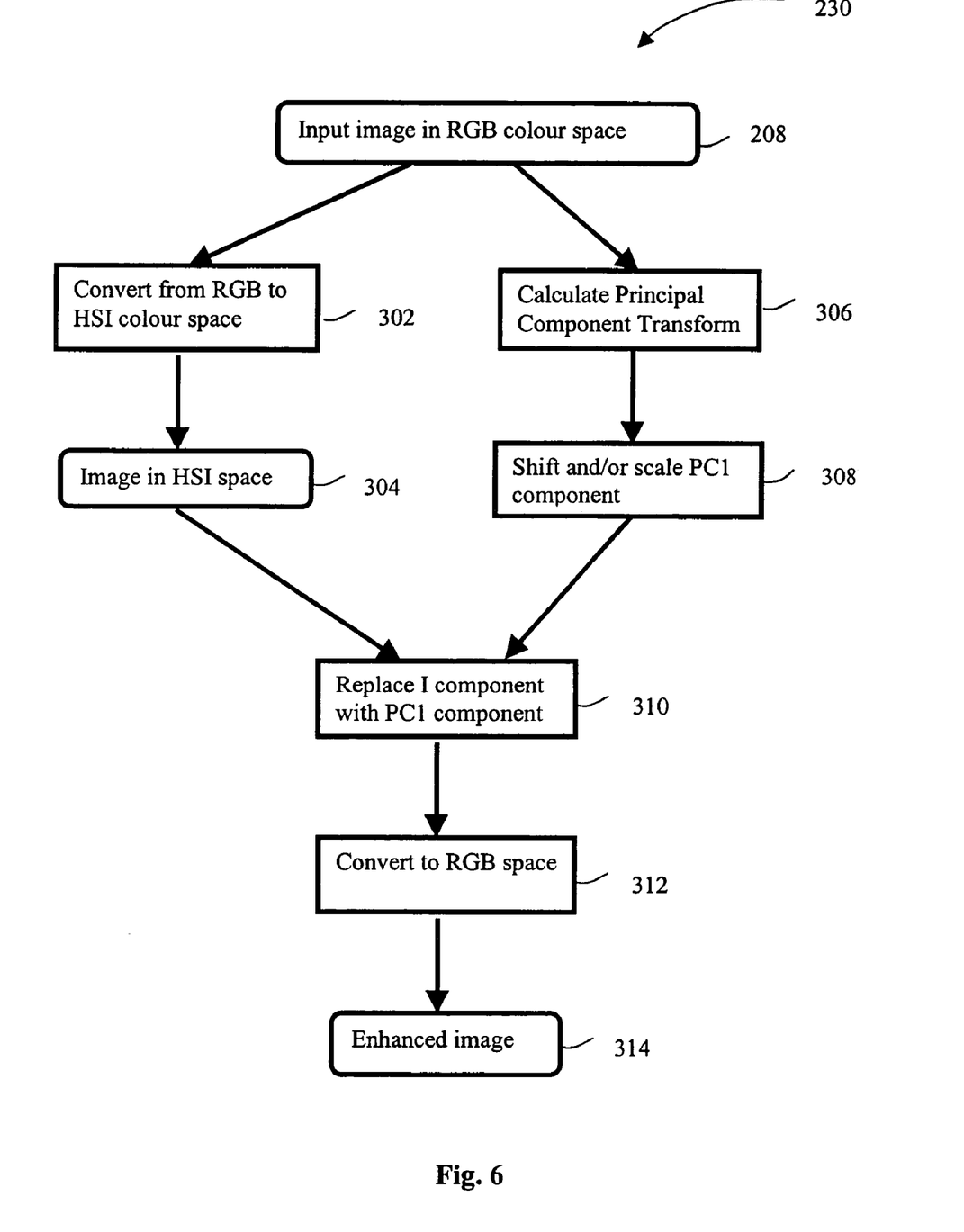
FIG. 6 shows a flow diagram of a method of enhancing an image, suitable for use in the method of FIG. 4.
Figure 10:
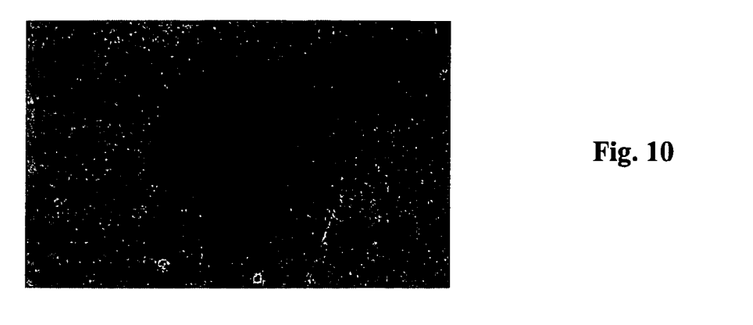
FIG. 10 shows the image of FIG. 8 after enhancement using the method of FIG. 6.

As an example of enhancement step 230, FIG. 10 shows the result of applying the enhancement method of FIG. 6 to the image of FIG. 8. Although poor reproduction of the images may obscure the effects, FIG. 10 exhibits greater contrast than FIG. 8, making it easier to distinguish the area of erythema.

Next, in step 232, the border of the wound 103 is defined. The border may be traced manually using a mouse 118 or light-pen when the image is displayed on display 114. Alternatively, known border detection methods may be used to automatically detect the border of the wound.

Figure 9:
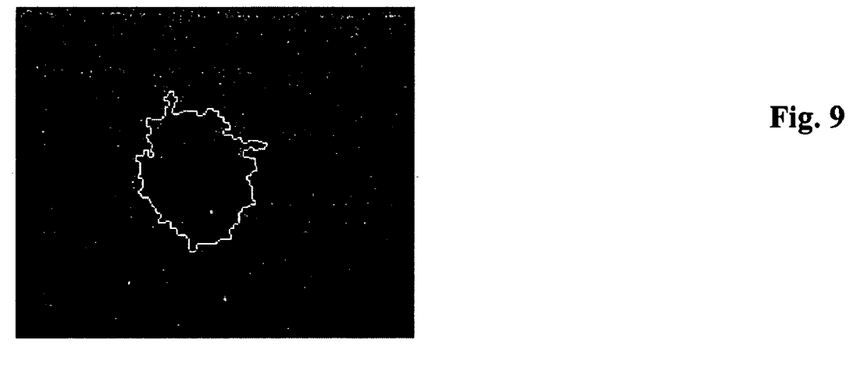
FIG. 9 shows the image of FIG. 8 with a boundary around the erythema that has been calculated using a manually-selected threshold.

It should be noted that the border of the wound 103 will generally be clearly visible, whereas the transition between the erythema area and surrounding skin may have low contrast. This is illustrated in FIG. 9, in which computer software has drawn a boundary between the erythema and the surrounding clear skin based on a tissue brightness threshold selected by an operator. Because the selection of the brightness threshold is highly subjective, the position of the boundary may vary between selections made by the same operator or by different operators.

Once the border of the wound has been defined, in step 234 a distance transform is performed on the area between the border of the wound and the edge of the field of view. The distance transform assigns a brightness value to each pixel of the image as a function of distance to the border of the wound. In a preferred arrangement, the chamfer 5-7-11 distance transformation is used. Details may be found, for example, in G. Borgefors, 'Distance Transformations in Digital Images', CVGIP 34, p 344-371 (1986).

Figure 5:
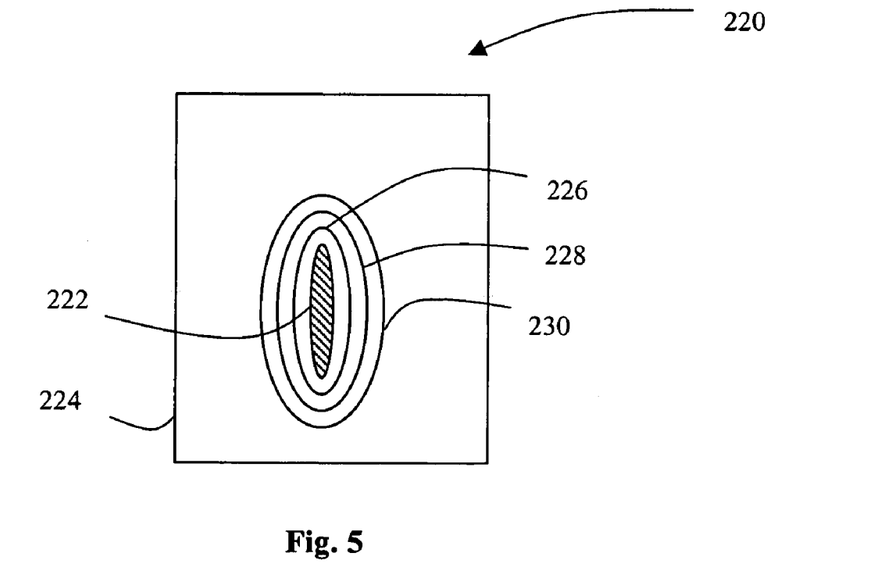
FIG. 5 is a schematic representation of a distance transform applied to an image of a wound.

In step 236 the output of the distance transform is used to divide the enhanced image into bands of pixels equidistant from the border of the wound. This is illustrated schematically in FIG. 5, in which an image 220 includes a wound 222. For ease of depiction, FIG. 5 shows only three bands of pixels 226, 228, 230 surrounding the wound 222. In practice further bands surround the wound 222 up to the edge of the field of view 224.

Figure 13:
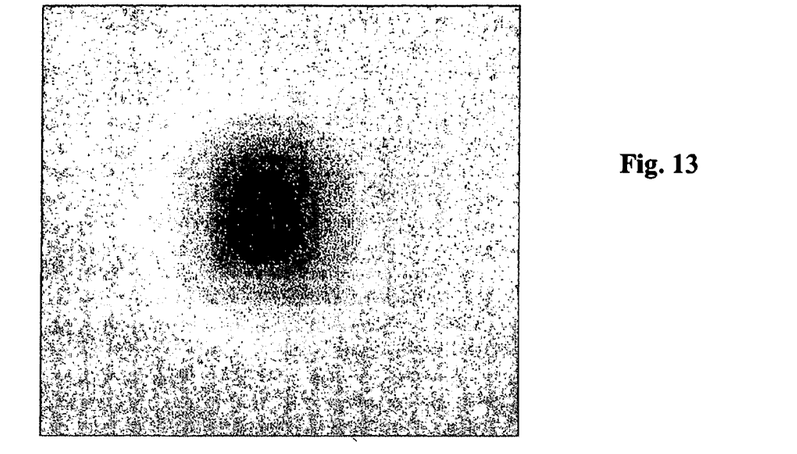
FIG. 13 shows an image of a wound surrounded by bands of pixels with the brightness of pixels in each band averaged.
Figure 14:
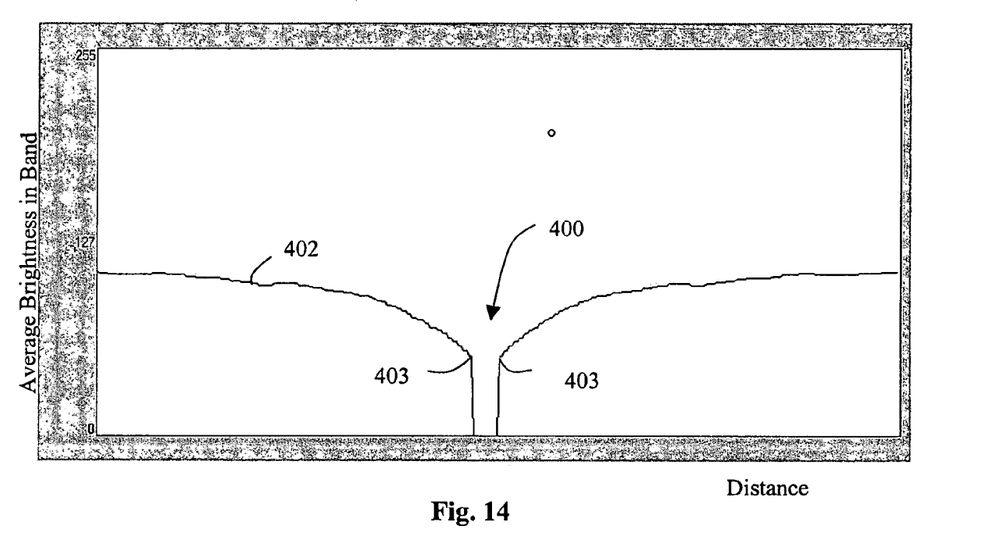
FIG. 14 shows a profile of brightness across the image of FIG. 13.

In step 238 the average brightness within each band is calculated. FIG. 13 shows an example of an image in which all the pixels in each band have been replaced by pixels having the average brightness of the band. The range of brightness shown in FIG. 13 is further illustrated in FIG. 14, which shows a profile 402 of brightness along a line drawn across the image of FIG. 13. The x-axis of FIG. 14 represents distance along the line and the y-axis of FIG. 14 represents the average brightness in a band. The gap 400 in the profile 402 indicates the wound, which has been assigned a brightness of zero within the border defined in step 232. The profile 402 has a minimum brightness 403 in the band adjacent the wound and then rises to reach a plateau towards the boundary of the image.

Returning to FIG. 4, in step 240 a boundary of erythema is determined by specifying a threshold value that is below the brightness of the clear skin at the periphery of the image. A suitable value of the threshold is 90% of the brightness at the image periphery. The band of pixels having an average brightness closest to the threshold value is defined to be the erythema boundary.

Figure 15:
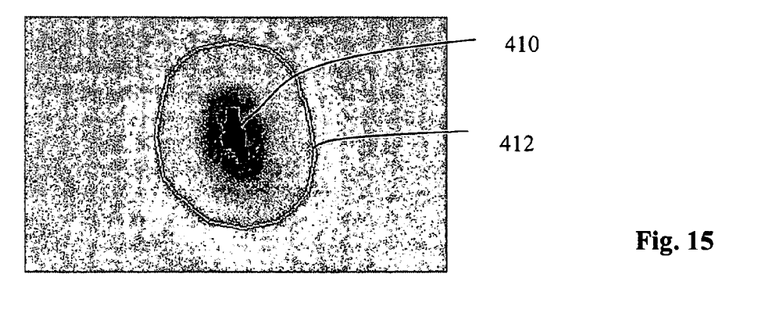
FIG. 15 shows a segmented wound image.

FIG. 15 shows an example of a boundary 412 enclosing an area of erythema around wound 410. The average brightness of pixels at the boundary 412 is 90% of the brightness of the area of clear skin towards the periphery of the image. The pixels of the boundary 412 have been replaced with pixels having a maximum brightness so that the boundary 412 is readily visible.

Figure 16:
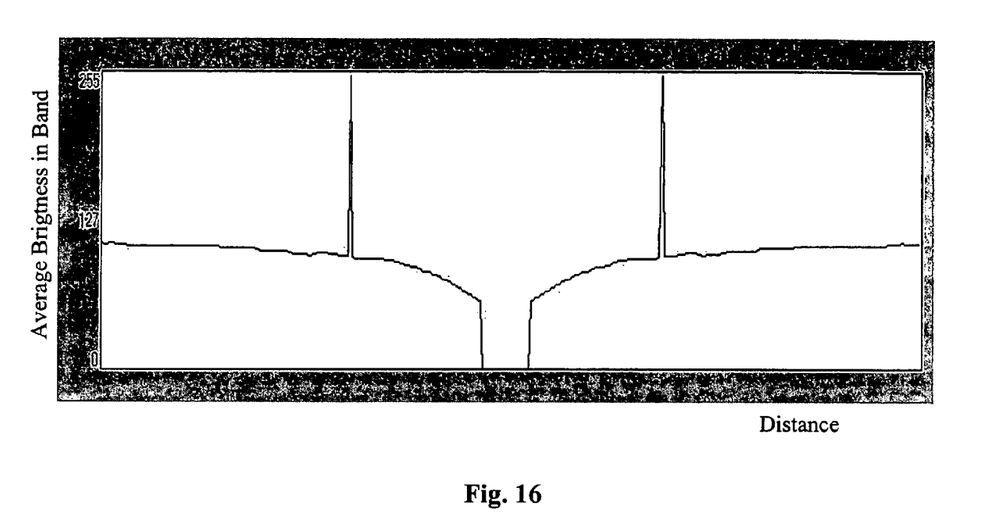
FIG. 16 shows a profile of brightness across the segmented image of FIG. 15.

The boundary is further illustrated in FIG. 16, which shows a profile of brightness along a line traversing FIG. 15. The erythema boundary 412 appears in FIG. 16 as two spikes 414 and 416, because the pixels of the boundary 412 have been replaced with pixels of maximum brightness.

Figure 17:
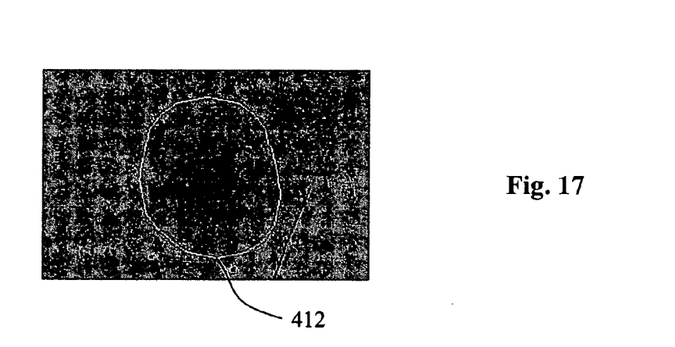
FIG. 17 shows the segmentation of FIG. 15 superimposed on the enhanced image of FIG. 10.

FIG. 17 shows the boundary 412 superimposed on the enhanced image of FIG. 10.

In the final method step of FIG. 4, a radius of the area of erythema is calculated using information from the distance transform performed in step 234.

The radius of erythema is useful as a single-valued indicator of the extent of erythema. When a wound is analysed over a period of time, the radius calculated at successive sample times provides a ready means of observing the rate of healing.

Alternatively, the diameter of the erythema or the area within the boundary of erythema can be used as a single-valued indicator of the extent of erythema.

FIG. 6 illustrates a preferred method of image enhancement, for use in method step 230 of FIG. 4. The input to the enhancement procedure is the image 208, where the image is defined in RGB (Red, Green, Blue) color space. Since image enhancement is more conveniently processed in the HSI (Hue, Saturation, Intensity) color space because it minimally distorts the perceived color, in step 302 the image 208 is converted from RGB to a description in HSI space. The output of step 310 is an image description 304 in HSI space. The Hue and Saturation components relate to the color of the image while the Intensity component is decoupled from the color information of the image.

In step 306 a principal component (PC) analysis of the image 208 is performed. In FIG. 6 step 306 is shown as occurring in parallel to step 302. Such a configuration is suitable for implementation in a distributed computing environment. However, where a single computer processor is used, steps 302 and 306 may be performed sequentially.

The first principal component axis calculated in step 306 is in the direction of maximum variance in the input data. The second PC axis captures most of the remaining variance, and any further principal component axes cater for any data falling outside the plane defined by the first and second axes. In the present instance where input data is defined in RGB space, there are three principal components. The PC transform may be calculated using commercially available software such as Matlab™ produced by MathWorks Inc. of Natick, Mass.

Next, in step 308, the PC1 component is shifted and/or scaled to fit a predefined dynamic range. When the enhanced image is to be presented on a computer screen, which normally uses eight bits to define each color component, it may be necessary to shift and/or scale the dynamic range of the PC1 value to fit into the range [0,255]. The dynamic range of the PC1 component prior to adjustment can stretch from negative values to positive values.

Once the dynamic range of the PC1 component has been mapped to the desired range, in step 310 the description of each point z in image 304, $(H_z, S_z, I_z)$, is replaced by $(H_z, S_z, PC1_z)$ for all z, where $PC1_z$ is the first principal component value as mapped to the desired dynamic range. Next, the image description is converted back to RGB space in step 312, yielding the enhanced image 314. The enhanced image 314 may be displayed on a suitable display device or may be used in further processing.

Figure 11:
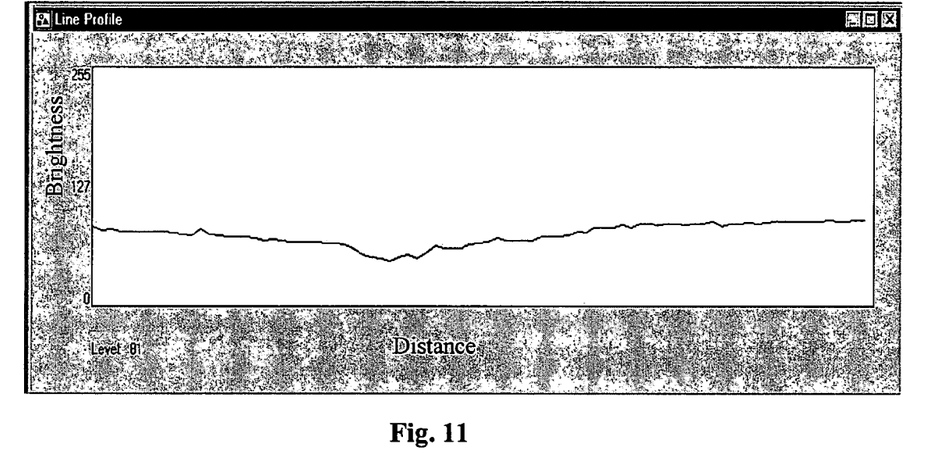
FIG. 11 shows a profile of image brightness along a line traversing an unenhanced image of a wound.
Figure 12:
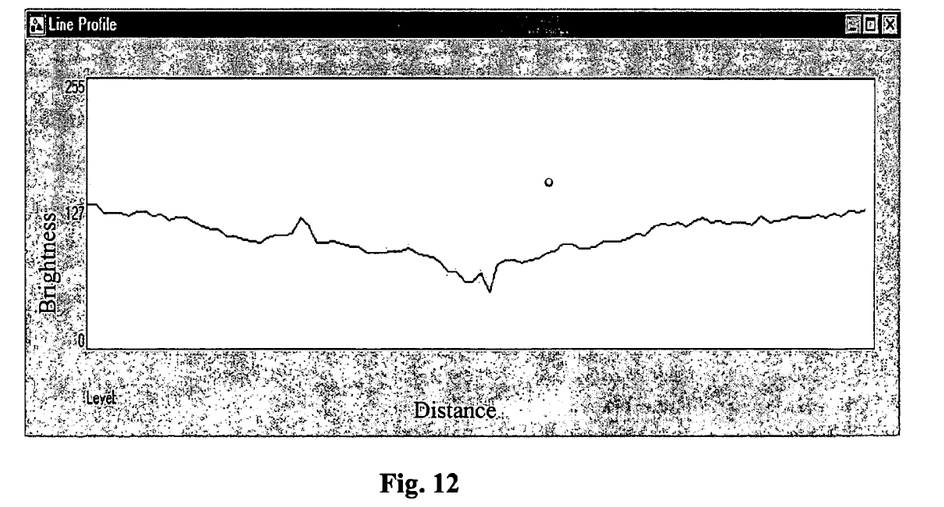
FIG. 12 shows a profile of image brightness along a line traversing an enhanced image of a wound.

The enhancement process of step 230 is further illustrated in FIGS. 11 and 12. FIG. 11 shows a profile of brightness along a line traversing an unenhanced image of skin with an area of erythema near the centre of the image. The erythema has lower brightness than clear skin. FIG. 12 shows a profile of brightness along a line traversing an enhanced image. It may be seen that the contrast, indicated by the vertical range from minimum brightness to maximum brightness, is greater for the enhanced profile.

In an alternative arrangement, a color component of the image 208 may be used instead of brightness in determining the boundary of the erythema. This is illustrated in FIGS. 18 and 19.

Figure 18:
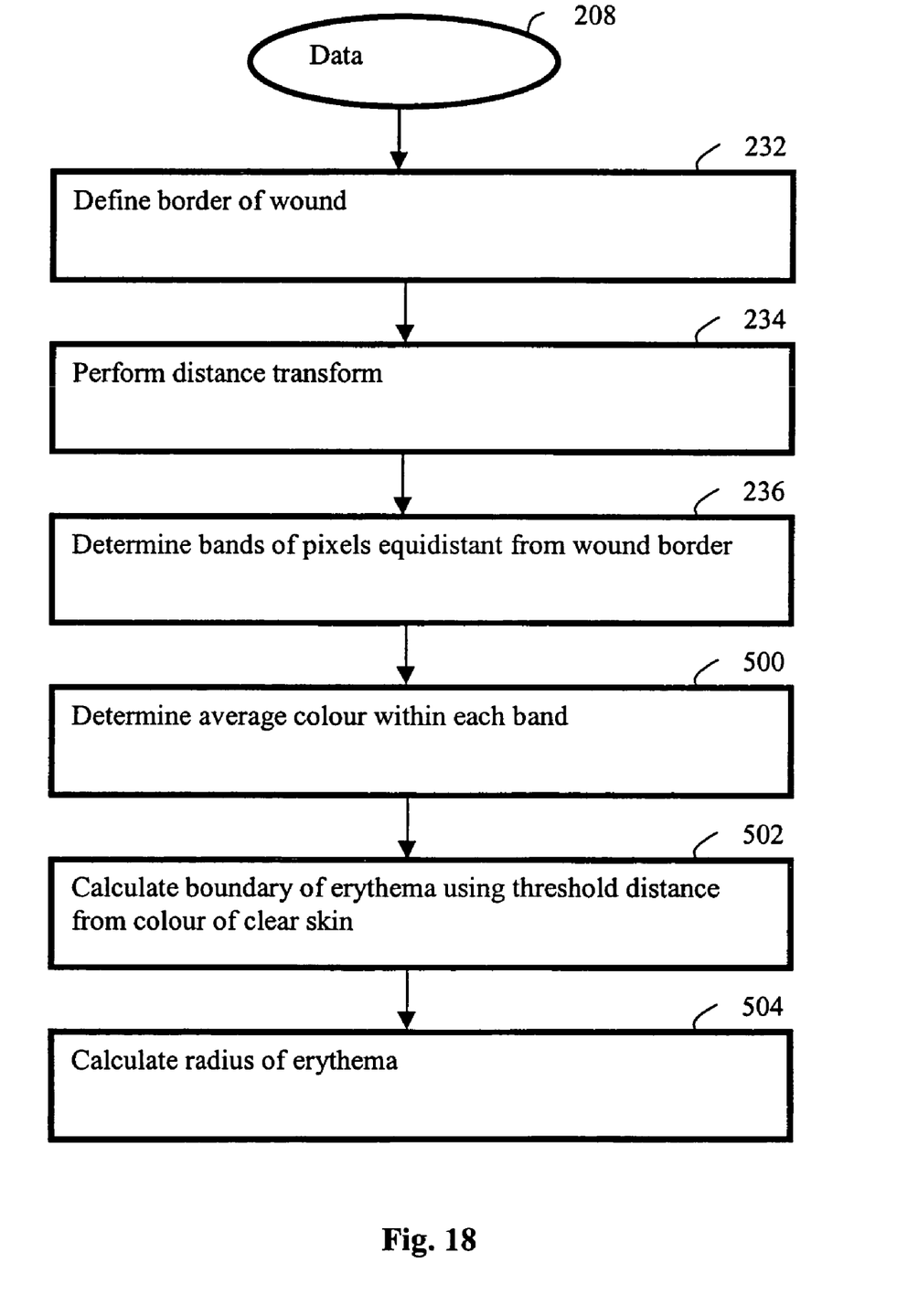
FIG. 18 shows a flow chart of an alternative method for quantifying the extent of erythema around a wound.
Figure 19:
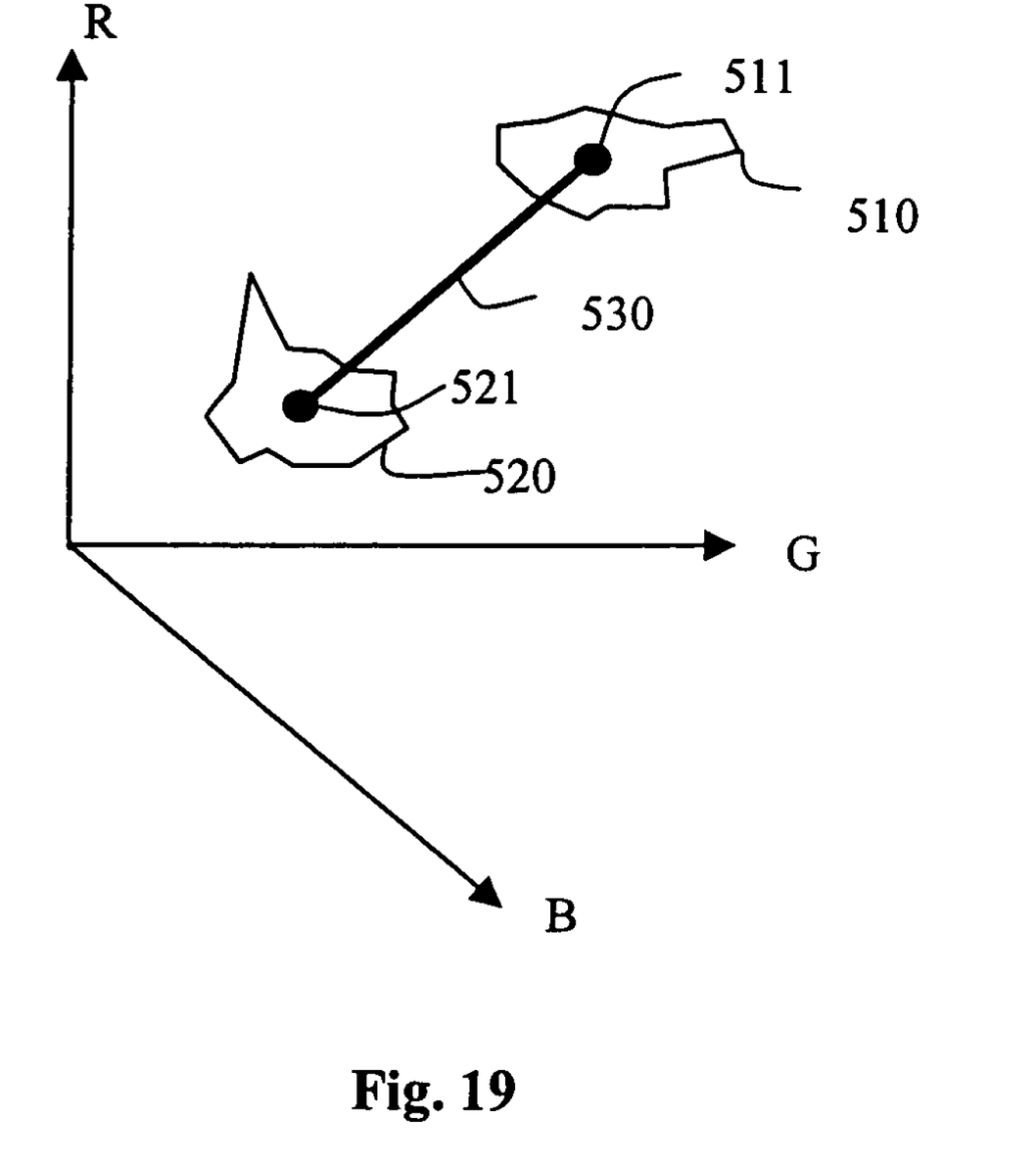
FIG. 19 illustrates a color distance measure for use in the method of FIG. 18.

Steps 232-236 of the flow chart of FIG. 18 are the same as the corresponding steps of the method of FIG. 4. In step 232 the border of the wound is defined and in step 234 a distance transform is performed on the area between the border of the wound and the edge of the field of view. In step 236 the result of the distance transform is used to define bands around the wound where the pixels within a band are equidistant from the wound boundary.

Next, in step 500, an average color is calculated for each band. Where the image is described in RGB space, the color of each pixel is defined by three values, ie a red component, a green component and a blue component. The color of each pixel corresponds to a point in RGB space, and the pixels in a band correspond to a cluster of points in RGB space. An average value of color for the band may be obtained by averaging each of the three color components for the pixels in a band. This is illustrated in FIG. 19, which shows a color space defined with respect to mutually orthogonal R, G and B axes. Region 510 of the color space contains all the pixels of a first band of pixels and the point 511 is the average color of the pixels in region 510. Region 520 contains the pixels of a second band of pixels and point 521 is the average color of the pixels in region 520.

An equivalent clustering may be performed if other color spaces are used to describe the image. For example, the CIE L*a*b* system may be employed. In this case the three components describing each pixel are L*, a* and b*.

A distance between bands may be defined as the Euclidean distance between the average colors of the bands. Thus, line 530 represents the distance between region 510 and region 520. Accordingly, each band of pixels may be defined in terms of the distance of the band to a reference band of pixels corresponding to clear skin.

In step 502 a band of pixels is chosen to represent the boundary of erythema, where the boundary is determined as the band closest to a threshold distance from the color of clear skin.

In step 504 the radius of erythema is calculated from the boundary derived in step 502. The radius is stored for future reference.

EXAMPLE

One application of the wound measurement techniques described above relates to the comparison of wound healing kinetics resulting from different therapies.

A small cut is made in the skin of a volunteer, causing erythema of the surrounding area. Images of the wound are captured at specified times after the wound was inflicted. For example, images may be taken half an hour, twenty-four hours and forty-eight hours after the skin was cut. Measuring the radius of the erythema provides a simple means of monitoring the progress of healing. Healing kinetics resulting from different methods of treating the wound may thus be readily compared.

Figure 20:
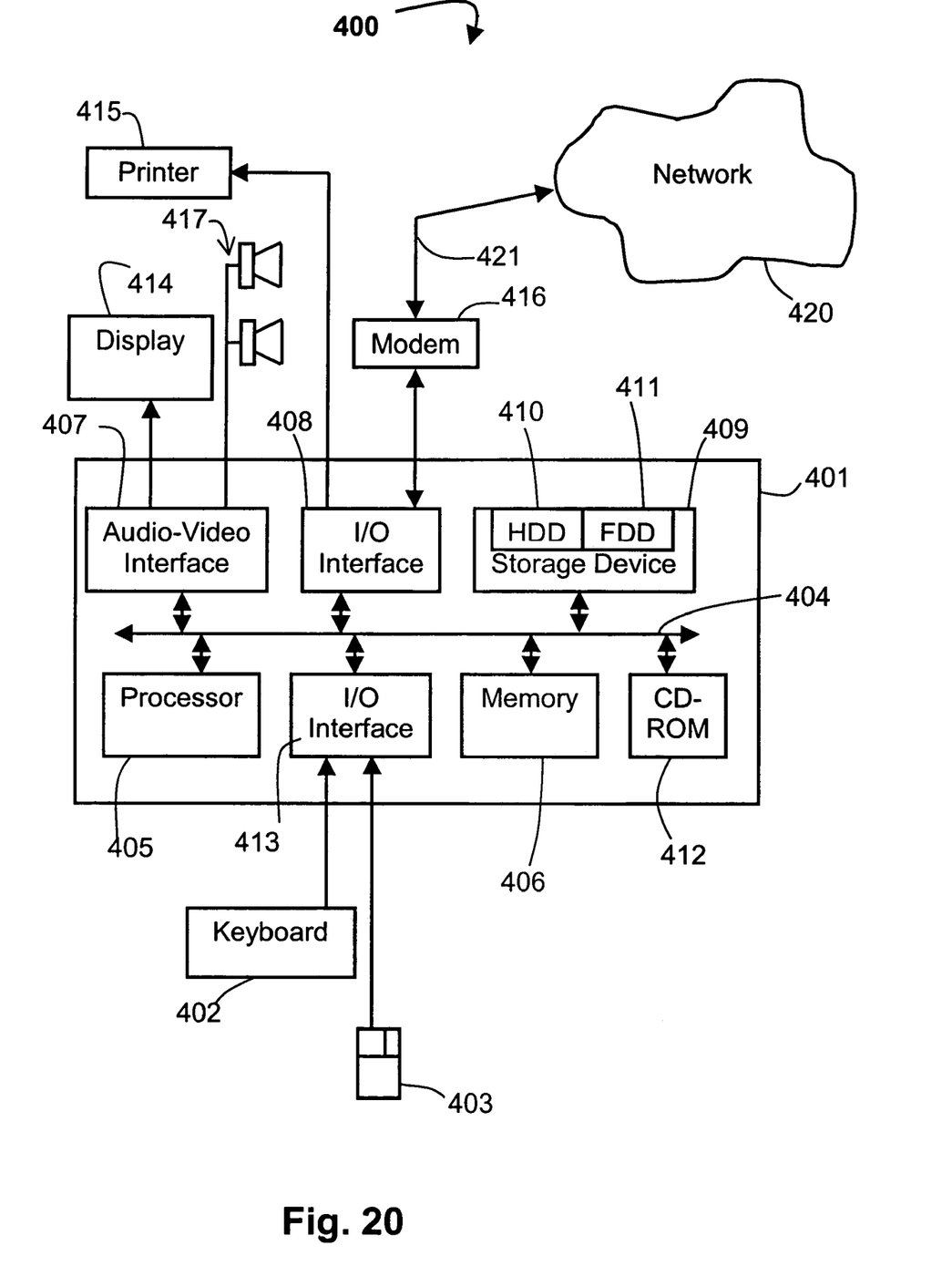
FIG. 20 is a schematic block diagram of a general purpose computer upon which arrangements described can be practiced.

The method of quantifying the extent of erythema is preferably practiced using a general-purpose computer system 400, such as that shown in FIG. 20 wherein the processes of FIGS. 3, 4, 6 and 18 may be implemented as software, such as an application program executing within the computer system 400. In particular, the method steps are effected by instructions in the software that are carried out by the computer. The instructions may be formed as one or more code modules, each for performing one or more particular tasks. The software may also be divided into two separate parts, in which a first part performs the erythema quantification methods and a second part manages a user interface between the first part and the user. The software may be stored in a computer readable medium, including the storage devices described below, for example. The software is loaded into the computer from the computer readable medium, and then executed by the computer. A computer readable medium having such software or computer program recorded on it is a computer program product. The use of the computer program product in the computer preferably effects an advantageous apparatus for quantifying the erythema around a wound.

The computer system 400 is formed by a computer module 401, input devices such as a keyboard 402 and mouse 403, output devices including a printer 415, a display device 414 and loudspeakers 417. A Modulator-Demodulator (Modem) transceiver device 416 is used by the computer module 401 for communicating to and from a communications network 420, for example connectable via a telephone line 421 or other functional medium. The modem 416 can be used to obtain access to the Internet, and other network systems, such as a Local Area Network (LAN) or a Wide Area Network (WAN), and may be incorporated into the computer module 401 in some implementations.

The computer module 401 typically includes at least one processor unit 405, and a memory unit 406, for example formed from semiconductor random access memory (RAM) and read only memory (ROM). The module 401 also includes a number of input/output (I/O) interfaces including an audio-video interface 407 that couples to the video display 414 and loudspeakers 417, an I/O interface 413 for the keyboard 402 and mouse 403 and optionally a joystick (not illustrated), and an interface 408 for the modem 416 and printer 415. In some implementations, the modem 416 may be incorporated within the computer module 401, for example within the interface 408. A storage device 409 is provided and typically includes a hard disk drive 410 and a floppy disk drive 411. A magnetic tape drive (not illustrated) may also be used. A CD-ROM drive 412 is typically provided as a non-volatile source of data. The components 405 to 413 of the computer module 401, typically communicate via an interconnected bus 404 and in a manner which results in a conventional mode of operation of the computer system 400 known to those in the relevant art. Examples of computers on which the described arrangements can be practised include IBM-PCs and compatibles, Sun Sparcstations or alike computer systems evolved therefrom.

Typically, the application program is resident on the hard disk drive 410 and read and controlled in its execution by the processor 405. Intermediate storage of the program and any data fetched from the network 420 may be accomplished using the semiconductor memory 406, possibly in concert with the hard disk drive 410. In some instances, the application program may be supplied to the user encoded on a CD-ROM or floppy disk and read via the corresponding drive 412 or 411, or alternatively may be read by the user from the network 420 via the modem device 416. Still further, the software can also be loaded into the computer system 400 from other computer readable media. The term "computer readable medium" as used herein refers to any storage or transmission medium that participates in providing instructions and/or data to the computer system 400 for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external of the computer module 401. Examples of transmission media include radio or infra-red transmission channels as well as a network connection to another computer or networked device, and the Internet or Intranets including e-mail transmissions and information recorded on Websites and the like.

The method of quantifying erythema around a wound may alternatively be implemented in dedicated hardware such as graphic processors, digital signal processors, or one or more microprocessors and associated memories.

INDUSTRIAL APPLICABILITY

It is apparent from the above that the arrangements described are applicable to the image processing and medical monitoring industries. The described arrangements provide a standardised means of quantifying the erythema around a wound, thereby enabling an objective monitoring of the wound healing process.

The foregoing describes only some embodiments of the present invention, and modifications and/or changes can be made thereto without departing from the scope and spirit of the invention, the embodiments being illustrative and not restrictive.

The invention claimed is:

1. A method of quantifying the extent of erythema around a wound of a patient, the method comprising the steps of:
    capturing an image that includes the wound, the erythema and surrounding skin;
    defining a border of the wound;
    performing a distance transform on an area of the image between the wound border and a boundary of the image to determine bands of pixels, wherein the pixels within each said band are equidistant from the wound border;
    calculating a representative value for each said band;
    defining a threshold level relative to the representative value of the surrounding skin;
    identifying an erythema boundary as the band having a representative value closest to the threshold level; and
    calculating a characteristic value to quantify the region within the erythema boundary.

2. A method according to claim 1 wherein the characteristic value is selected from the group consisting of:
    a radius of the erythema boundary;
    a diameter of the erythema boundary; and
    an area of the region within the erythema boundary.

3. A method according to claim 1 wherein the representative value is selected from the group consisting of:
    an average brightness; and
    an average color.

4. A method according to claim 1, further comprising the step of applying a clear fluid to the patient before the image capture step to reduce specular reflections from the patient.

5. A method according to claim 4 wherein the clear fluid is a gel.

6. A method according to claim 1, wherein cross-polarised light is used in the image capture step to reduce specular reflections from the patient.

7. A method according to claim 1, further comprising the step of enhancing the image to increase contrast.

8. A method according to claim 7 wherein the image is defined with respect to an intensity component and said enhancement step comprises replacing the intensity component with a principal component value.

9. A method of monitoring a wound of a patient, the method comprising the steps of:
    capturing a time series of images, each said image including the wound, erythema around the wound and clear skin surrounding the erythema;
    for each said image, defining a border of the wound;
    for each said image, performing a distance transform on an area of the image between the wound border and a boundary of the image to determine bands of pixels, wherein the pixels within each said band are equidistant from the wound border;

for each image, calculating a representative value for each said band;

defining a threshold level relative to the representative value of the surrounding clear skin;

for each image, identifying an erythema boundary as the band having a representative value closest to the threshold level;

for each image, calculating a characteristic value to quantify the region within the erythema boundary; and comparing said characteristic values to monitor changes in the extent of erythema around the wound.

10. A method according to claim 9 wherein the characteristic value is selected from the group consisting of:
a radius of the erythema boundary;
a diameter of the erythema boundary; and
an area of the region within the erythema boundary.

11. A method according to claim 9 wherein the representative value is selected from the group consisting of:
an average brightness; and
an average color.

12. Apparatus for quantifying the extent of erythema in an image including a wound, erythema around the wound and clear skin surrounding the erythema, the apparatus comprising:
means for defining a border of the wound;
means for performing a distance transform on an area of the image between the wound border and a boundary of the image to determine bands of pixels, wherein the pixels within each said band are equidistant from the wound border;
means for calculating a representative value for each said band;
means for identifying an erythema boundary as the band having a representative value closest to a threshold level; and
means for calculating a characteristic value to quantify the region within the erythema boundary.

13. Apparatus according to claim 12 wherein the characteristic value is selected from the group consisting of:
a radius of the erythema boundary;
a diameter of the erythema boundary; and
an area of the region within the erythema boundary.

14. Apparatus according to claim 12 wherein the representative value is selected from the group consisting of:
an average brightness; and
an average color.

15. Apparatus according to claim 12, further comprising means for enhancing the image to increase contrast.

16. Apparatus according to claim 15 wherein the image is defined with respect to an intensity component and said means for enhancing the image acts to replace the intensity component with a principal component value.

17. A computer program product comprising computer-readable program code recorded on a computer-readable recording medium, for controlling the operation of a data processing apparatus on which the computer program code executes to perform a procedure to quantify the extent of erythema in an image including a wound, erythema around the wound and clear skin surrounding the erythema, the procedure comprising the steps of:
defining a border of the wound;
performing a distance transform on an area of the image between the wound border and a boundary of the image to determine bands of pixels, wherein the pixels within each said band are equidistant from the wound border;
calculating a representative value for each said band;
identifying an erythema boundary as the band having a representative value closest to a threshold level; and
calculating a characteristic value to quantify the region within the erythema boundary.

18. An apparatus for quantifying the extent of erythema around a wound of a patient, the apparatus comprising:
a storage device for storing an image that includes the wound, the erythema and surrounding skin; and
a processor coupled to the storage device and programmed to:
define a border of the wound;
perform a distance transform on an area of the image between the wound border and a boundary of the image to determine bands of pixels, wherein the pixels within each said band are equidistant from the wound border;
calculate a representative value for each said band;
define a threshold level relative to the representative value of the surrounding skin;
identify an erythema boundary as the band having a representative value closest to the threshold level; and
calculate a characteristic value to quantify the region within the erythema boundary.

* * * * *